US008561612B2

(12) United States Patent
Heinonen (10) Patent No.: US 8,561,612 B2
(45) Date of Patent: Oct. 22, 2013

(54) METHOD AND SYSTEM FOR MONITORING PATIENT'S BREATHING ACTION RESPONSE TO CHANGES IN A VENTILATOR APPLIED BREATHING SUPPORT

(75) Inventor: Erkki Paavo Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 1474 days.

(21) Appl. No.: 12/052,174

(22) Filed: Mar. 20, 2008

(65) Prior Publication Data

US 2008/0230065 A1    Sep. 25, 2008

(30) Foreign Application Priority Data

Mar. 22, 2007   (EP) ..................... 07104653

(51) Int. Cl.
*A61M 16/00* (2006.01)
*A62B 7/00* (2006.01)

(52) U.S. Cl.
USPC ............. 128/204.23; 128/204.21; 128/204.18

(58) Field of Classification Search
USPC ............. 128/200.24, 204.18, 204.21–204.23; 600/529, 531, 532
See application file for complete search history.

(56) References Cited

U.S. PATENT DOCUMENTS

| 4,211,239 | A | * | 7/1980 | Raemer et al. | 600/529 |
| 4,233,842 | A | * | 11/1980 | Raemer et al. | 73/861.04 |
| 4,917,108 | A | * | 4/1990 | Mault | 600/531 |
| 5,072,737 | A | * | 12/1991 | Goulding | 600/531 |
| 5,429,123 | A | * | 7/1995 | Shaffer et al. | 128/204.23 |
| 6,581,595 | B1 | * | 6/2003 | Murdock et al. | 128/204.18 |
| 2006/0005836 | A1 | * | 1/2006 | Brugnoli | 128/205.11 |
| 2006/0201507 | A1 | * | 9/2006 | Breen | 128/204.22 |
| 2007/0173729 | A1 | * | 7/2007 | Fisher et al. | 600/532 |
| 2007/0181126 | A1 | * | 8/2007 | Tolmie et al. | 128/204.21 |
| 2008/0127977 | A1 | * | 6/2008 | Orr et al. | 128/204.22 |

FOREIGN PATENT DOCUMENTS

| EP | 0 753 320 A1 | 1/1997 |
| EP | 0 833 156 A1 | 1/1998 |
| WO | WO 00/45702 A1 | 8/2000 |

* cited by examiner

*Primary Examiner* — Justine Yu
*Assistant Examiner* — Valerie L Skorupa
(74) *Attorney, Agent, or Firm* — Global Patent Operation; Marc A. Vivenzio (57) ABSTRACT

A method for monitoring patient's breathing action response to changes in a ventilator applied breathing support, where a) a desired target range for a breathing gas indication of O2-consumption for the patient is first determined, after which b) the ventilator applied breathing support is changed, and c) the breathing gas indication of O2-consumption of said patient is measured and d) compared with the desired target range. At least the steps b)-d) are repeated to maintain the measured breathing gas indication of O2-consumption of said patient within the desired target range. A system for monitoring a patient's breathing action is also provided.

9 Claims, 6 Drawing Sheets

METHOD AND SYSTEM FOR MONITORING PATIENT'S BREATHING ACTION RESPONSE TO CHANGES IN A VENTILATOR APPLIED BREATHING SUPPORT

CROSS-REFERENCE TO RELATED APPLICATIONS

This application claims the right of priority, under 35 USC 119 (a)-(d), to the earlier filing date of co-pending European patent application serial number: 07104653.6, filed 22 Mar. 2007. The basis for this claim of priority is the European Community's membership in the World Trade Organization.

BACKGROUND

1. Field of the Invention

Embodiments of the invention relates to a method, system and computer program product for monitoring patient's breathing action response to changes in a ventilator applied breathing support, and in addition for assessing a readiness of a patient to be weaned from a ventilator in a weaning process and for adjusting the ventilator applied breathing support.

2. Description of Prior Art

Weaning the patients from artificial ventilation is among the most difficult questions regarding intensive care ventilation. Patients encountering weaning problems have often been ventilated to cure from the primary illness more than 48 hours before the ventilator weaning can be considered. Within the stay on ventilator support some patients develop ventilator dependency and they cannot maintain breathing of their own. This dependency may prolong the stay on ventilator therapy manifold in comparison with that needed for curing the primary illness. Prolonged ventilation increases risk for lung inflammation known as ventilator induced lung injury (VILI). Even worse, inflammatory mediator may spread from the lungs to other organs developing multiple-organ-failure. Mortality of those patients is high. Therefore, minimizing the stay on ventilator is primary goal for intensive care.

Methods for assessing the readiness for weaning are known from the prior art. However, assessing the readiness for weaning varies between clinics and so does the average stay on ventilator as well. Studies of current practices have revealed that lack of intensive care personnel correlates with delayed weaning promoting the need for systematic process to wean from ventilator. Clinical research on such processes focuses on three separate weaning phases: (1) screening to assess curing from primary illness indicating readiness to consider weaning, (2) evaluate patients ability to maintain sufficient gas exchange without ventilator support, and (3) extubation.

Screening proposals are often based on a set of laboratory and respiratory parameters that have to stay within specified range to consider weaning. To evaluate patient's ability to breath without ventilator various prior art protocols are used, like stepwise ventilator support reduction, or T-tube trial, where patient is just disconnected from ventilator. The prior art methods however share the problem of sensitive indicators. Final decision to extubate the patient depends finally on patient's ability to maintain airways open.

Reasons contributing to weaning problems have also been on clinical research. One leading hypothesis is respiratory muscle atrophy that develops rapidly in the unused muscles during artificial ventilation. Spontaneous breathing supports maintenance of muscular strength, but on sedated patient this requires continuous regulation of the ventilator support for moderate exercise level. For this purpose automatic control of ventilator settings based on measured patient values have been introduced (Dojat M, Harf A, Touchard D, Lemaire F, Brochard L: Clinical Evaluation of a Computer-controlled Pressure Support Mode Am J Respir Crit. Care Med Vol 161. pp 1161-1166, 2000). This prior art system regulates the ventilator support pressure to maintain spontaneous breathing frequency as primary control parameter on preset range, and tidal volume above minimum level as well as end-tidal $CO_2$ concentration below maximum as limiting parameters. Basically in this kind of systems the pressure support is increased if the breathing frequency will be too fast, and decreased, if the breathing frequency will be too slow, respectively. However, the prior art system also automatically suggest considering weaning from ventilator when the ventilator support pressure reduces below predetermined limit for predetermined time.

There are, however, some disadvantages relating to the prior art systems, such as the vague correlation of respiration rate or frequency to the gas exchange the ventilation should maintain. Assessing the respiration frequency could be comfortable when considering the average of number of patients, but often not for an individual patient. This may overstress a patient and delay the weaning unnecessarily. Therefore the prior art method cannot be applied on difficult to wean patients.

SUMMARY OF THE INVENTION

Embodiments of the invention aim to overcome the problems relating to the known prior art, such as providing a method, which measures the strength of patient breathing effort during changing ventilator applied breathing support. Embodiments of this invention are applied in assessing patient's readiness to be weaned from a ventilator in a weaning process and controlled training of patient's respiratory muscles.

In an embodiment, this aim is achieved by determining a breathing gas indication of $O_2$-consumption of a patient, when a ventilation support for the patient is decreased. In more details, if the support can be decreased to a predetermined target level for a predetermined time so that at the same time the breathing gas indication of $O_2$-consumption of said patient reveals that the $O_2$-consumption remains below predetermined $O_2$-consumption, weaning of the patient from the ventilator breathing support is probable.

Embodiments of the invention relate to a method for monitoring patient's breathing action response to ventilator applied breathing support.

Further embodiments of the invention relate to a system for monitoring patient's breathing action response to ventilator applied breathing support, the system comprising a ventilator, controller and gas sensor.

In addition embodiments of the invention relate to a computer program product for monitoring patient's breathing action response to ventilator applied breathing support.

The following abbreviations are used in this description and/or in the appended claims:

$VO_2$ $O_2$-consumption
$VCO_2$ $CO_2$-elimination
$EtO_2$ end-tidal $O_2$-concentration
$FiO_2$ inspired $O_2$-concentration
$EtCO_2$ end-tidal $CO_2$-concentration It is known that in the alveoli of the lungs carbon dioxide ($CO_2$) and oxygen ($O_2$) gases are exchanged between the breathing gases and pulmonary circulation. Difference in the gas partial pressure in blood and alveoli is the driving force for the gas exchange. Normally $CO_2$ partial pressure is high in blood compared to alveoli and $CO_2$ will be washed out from the circulation. Respectively, $O_2$-pressure of the alveoli is high compared to blood and as $O_2$ is taken up into the circulation.

In the body $O_2$ is consumed in organ- and muscle work producing $CO_2$. Ventilation supplies new $O_2$ to the alveoli and removes the $CO_2$ to maintain the alveolar gas pressures. Muscular work, including the respiratory muscles, increases patient $O_2$-consumption that increases the $CO_2$-production as well. Normal respiratory control would increase ventilation to maintain the blood and alveolar partial pressures for $O_2$ and $CO_2$, when needed.

Thus, measuring the gas exchange parameters of $VO_2$ ($O_2$-consumption) and/or $VCO_2$ ($CO_2$-elimination) when transferring responsibility of ventilation from a ventilator to a patient are direct indicators of the patient's ability to take over this responsibility: Increasing $VO_2$ indicates increased work of breathing of the patient, when the breathing support for the patient is decreased. Respectively this will—or at least should—result to increased $VCO_2$.

For a patient, who is not able to take over the breathing responsibility, the increased work of breathing is not efficient for producing sufficient ventilation. Thus $CO_2$ is not washed out but accumulates in body storages instead, and the $VCO_2$-increment may be small compared to $VO_2$-increase, or even decrease. This will make the patient to try harder to breath resulting to further increased $VO_2$. Would this increase be too high, muscle fatigue develops. Thus $VCO_2$-change mismatching with $VO_2$-change indicates demand for increasing breathing support.

In addition to wean a patient from the artificial ventilation, an embodiment of the invention can be used to train muscular activity of patients still needing at least partial breathing support. Such training would preserve the respiratory muscle strength for the forthcoming weaning. The training may be daily repetitive period of e.g. 15 min, 30 min or 1 hour, or even longer, depending on the patient's state. During this period ventilator support is advantageously gradually reduced until $VO_2$ is increased on predetermined level, or alternatively, in predetermined ratio from the baseline $VO_2$ in full ventilation support. Rest of the day under full ventilation support gives relaxation to the patient compensating for the muscular activity period.

According to an embodiment of the invention the ventilator breathing support is decreased in the training advantageously so that the exercise will be on a moderate level and the breathing support is kept in a certain level so that fatigue of the respiratory muscles is avoided, but breathing muscle activity and work condition is still maintained and in this way also trained and strengthened. In this invention the ventilation support is advantageously controlled to maintain these gas exchange parameters on preset level in order to achieve desired results.

According to an embodiment of the invention $VO_2$-consumption and $CO_2$-elimination is advantageously measured from the breathing gases of the patient by integrating the product of breathing gas flow and gas concentration over time.

A measurement of the breathing gases is described now in more details. For simplicity, assuming constant alveolar ventilation in a ventilator support reduction, increased $O_2$-consumption increases alveolar $O_2$-extraction into circulation. This decreases the alveolar $O_2$-concentration, which can be measured as end-tidal $O_2$-concentration ($EtO_2$). Because inspired $O_2$-concentration ($FiO_2$) may be varied, the decrease caused by work of breathing can be measured as the oxygen difference ($DO_2=FiO_2-EtO_2$). Respectively, increased metabolism increases the $CO_2$-elimination, and with unchanged ventilation the alveolar $CO_2$-concentration increases as a result of increased blood $CO_2$ partial pressure. This increase can be measured as end-tidal $CO_2$-concentration ($EtCO_2$). Because inspired $CO_2$-concentration is practically zero that does not need to be taken into consideration. Patient tends to compensate the increased $CO_2$-concentration and $O_2$-demand by enhancing alveolar ventilation. This will however increase the work of breathing further and the tendency of $DO_2$ increase continues.

In modern ventilators the breathing support or pressure support is applied typically in a form of elevated breathing pressure when a spontaneous breathing action is detected. The amount of breathing support is then regulated by adjusting the magnitude of pressure elevation.

Because the alveolar $O_2$ reservoir is much smaller than body buffering capacity of $CO_2$, the $DO_2$ is more sensitive indicator of the changes in work of breathing, and actually if patient is successful in increasing the alveolar ventilation, the $EtCO_2$ may level out, presenting positive indication of patient ability to maintain ventilation with the current ventilator support. While breathing support is reduced to predetermined limit, e.g. 5 $cmH_2O$ continuous airway pressure, while maintaining the $DO_2$ and $EtCO_2$ below threshold limits suggests patient readiness for weaning. Applicable limit for $DO_2$ could be 5.6-5.7 vol % and for $EtCO_2$ 5.1 vol %. Alternatively, instead of considering absolute value of $DO_2$ and $EtCO_2$, that may vary from patient to patient, evaluation can be based on the changes of $DO_2$ and $EtCO_2$ related to change in breathing support reduction. This will then directly correlate with the change in patient's work of breathing with the amount of breathing work transferred from the ventilator to the patient.

On contrary, if despite of increased work of breathing and increased $DO_2$ the patient is unable to respond with alveolar ventilation to the metabolic demand, $EtCO_2$ will also increase. This indicates insufficient ventilator support. In trials testing patient's ability to breathe, combination of high $DO_2$ (e.g. over 5.6%-5.7%) and high $EtCO_2$ (e.g. above 5.1%) is strong predictor of patient's inability maintain sufficient breathing and suggest immediate increase of the support pressure. As well here, instead of considering absolute values, change of the parameters in relation to the change in breathing support can be uses as indicator.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

BRIEF DESCRIPTION OF THE DRAWINGS

Next embodiments of the invention will be described in greater detail with reference to exemplary embodiments in accordance with the accompanying drawings, in which.

DETAILED DESCRIPTION

Figure 1A:
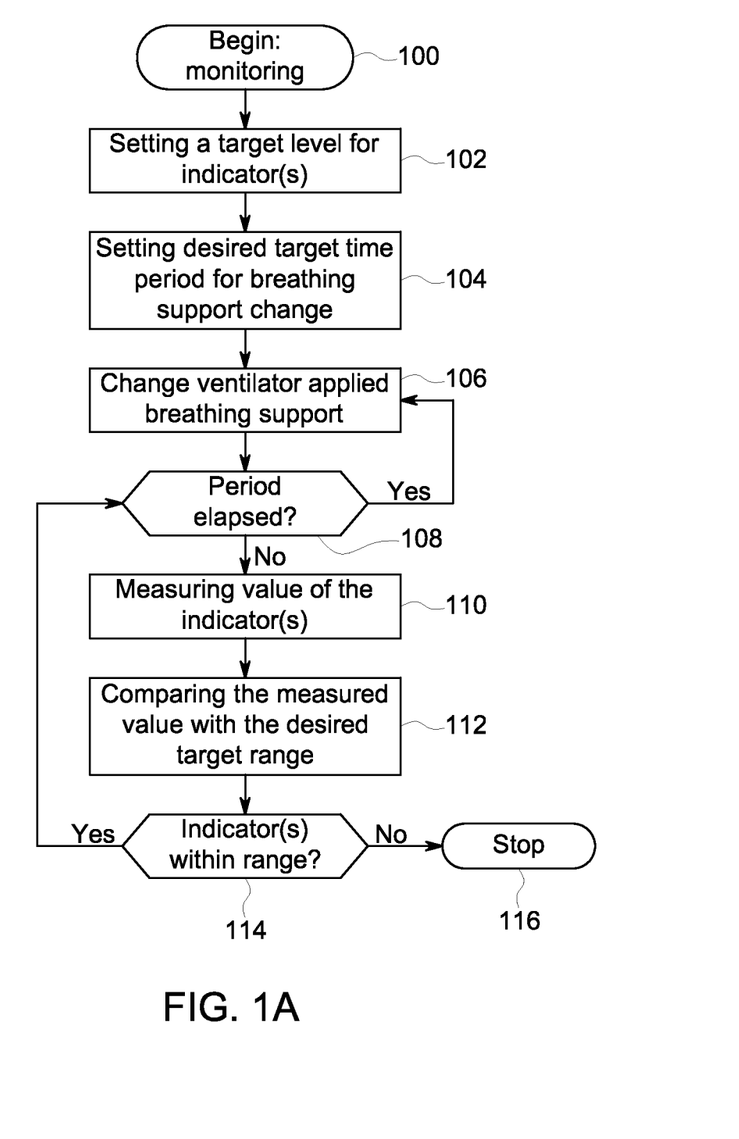
FIG. 1A illustrates a flow chart of an exemplary method for monitoring patient's breathing action response to changes in a ventilator applied breathing support according to an advantageous embodiment of the invention.

FIG. 1A illustrates a flow chart of an exemplary method 100 for monitoring patient's breathing action response to changes in a ventilator applied breathing support according to advantageous embodiment of the invention, where in step 102 desired target range of at least one indicator (such as an indicator of $O_2$-consumption) for the patient is set, after which also desired target time period for breathing support change can be set in step 104. Next in step 106 ventilator applied breathing support is changed.

In step 108 duration of the period set in step 104 is checked, whether it is elapsed. If not, the method is continued in step 110, where value of the indicator is measured. Comparing the measured indicator value with the desired target range is done in step 112. Whether the measured indicator value is within the range, the method is continued again in step 108. Otherwise the method is ended in step 116. Alternatively, the method may also progress to step 106 to change the breathing support to preserve the measured indicator value back to the target range. If the period has elapsed in step 108, the method can be continued again in step 106. In some embodiment of the invention the performing of the method can also be stopped, when the period has elapsed.

Figure 1B:
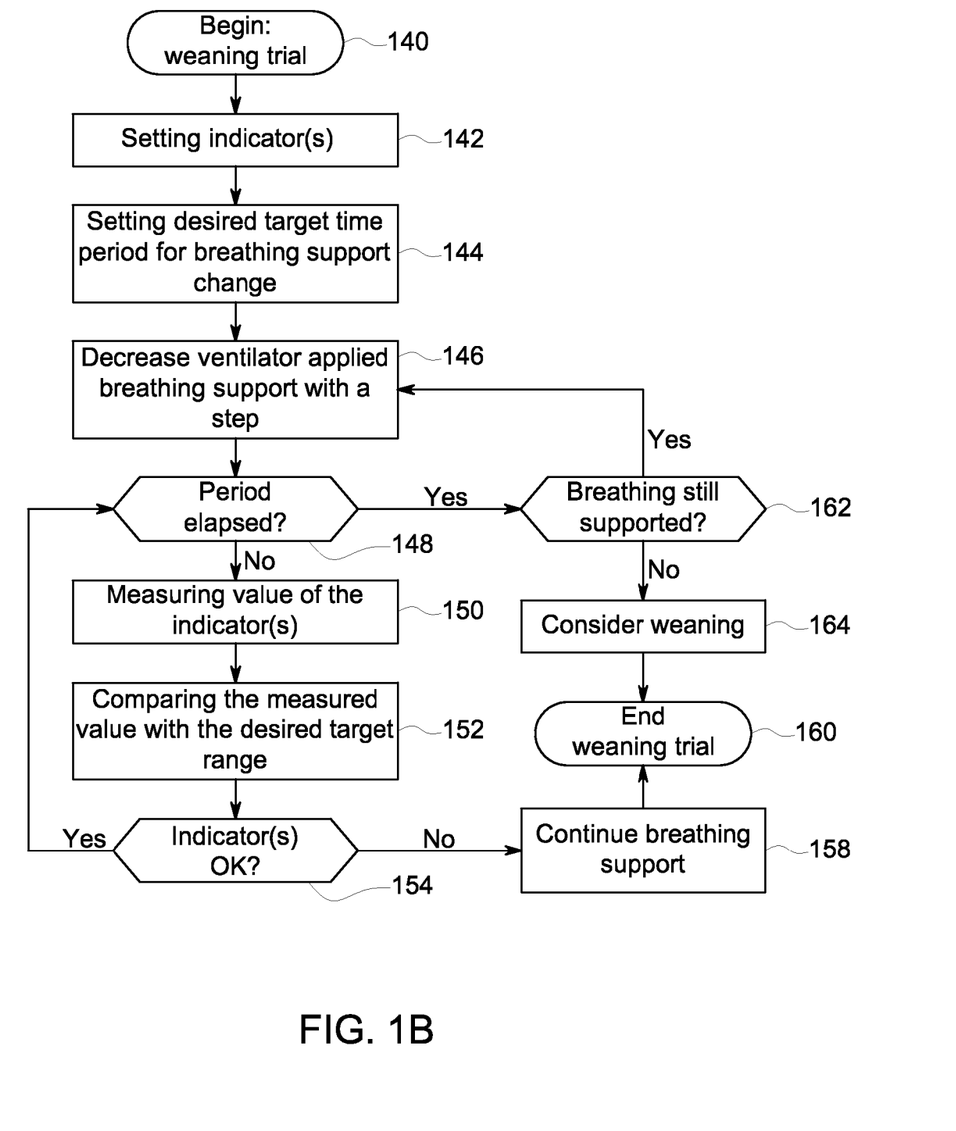
FIG. 1B illustrates a flow chart of an exemplary method for monitoring patient's breathing action and assessing a readiness of the patient to be weaned from a ventilator in a weaning process according to an advantageous embodiment of the invention.

FIG. 1B illustrates a flow chart of an exemplary method for assessing a readiness of the patient to be weaned from a ventilator in a weaning process according to an advantageous embodiment of the invention, where the weaning trial is begun in step 140. In step 142 desired target range of at least one indicator (such as maximum for an indicator of $O_2$-consumption) for the patient is set, after which also desired target time period for breathing support change can be set in step 144. Next in step 146 ventilator applied breathing support is decreased with a step.

Whether the period set in step 144 is not elapsed in step 148, the method is continued in step 150, where value of the indicator is measured and the measured indication value is compared with desired target range (set in step 142) in step 152. If the indicator is in the allowable range (for example the indicator of $O_2$-consumption is less than the maximum set in step 142) in step 154, the method is continued again in step 148. Otherwise, if the indicator is not in the allowable range in step 154, breathing support is continued in step 158 and the weaning trial is ended in step 160.

However, if the period has elapsed in step 148 and breathing is still supported (step 162), the method is advantageously continued again in step 146. Otherwise, if breathing is not supported anymore (step 162), weaning can be considered in step 164.

In other words, ventilator applied support is needed, if, when changing the ventilator applied breathing support, the breathing gas indication of $O_2$-consumption of said patient reveals that the $O_2$-consumption don't remain in the determined desired target range.

Figure 1C:
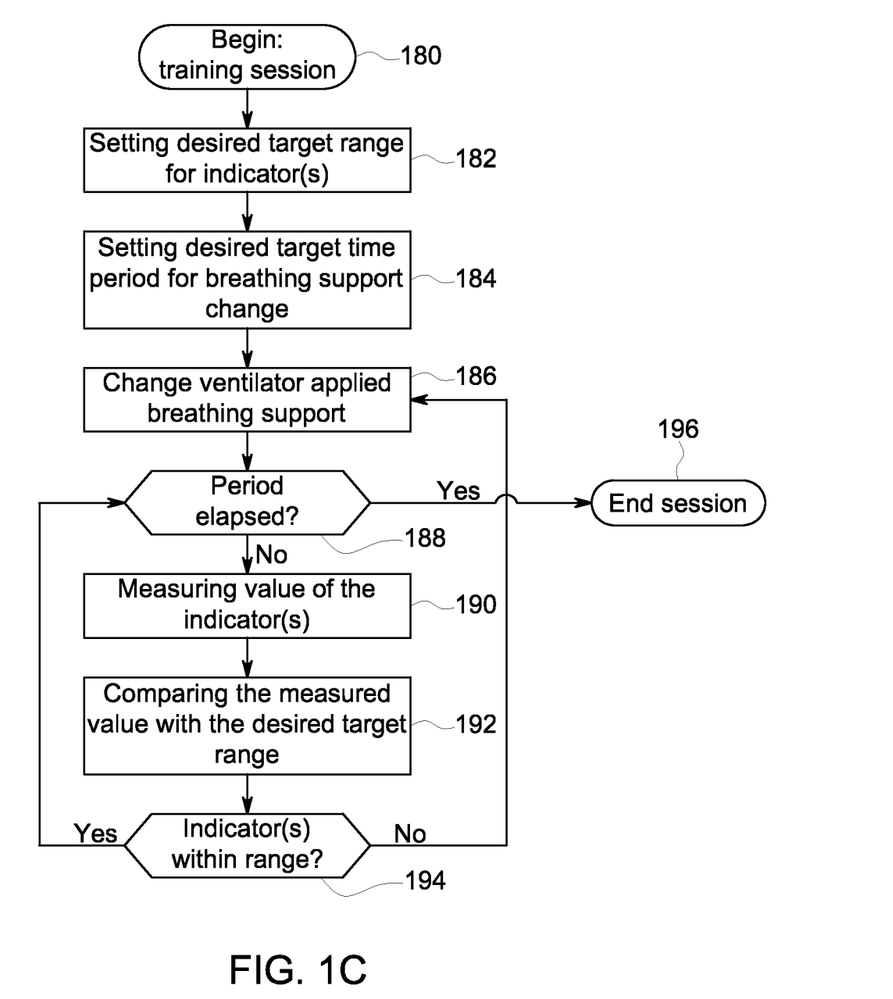
FIG. 1C illustrates a flow chart of an exemplary method for training muscular activity of patients still needing at least partial breathing support according to an advantageous embodiment of the invention.

FIG. 1C illustrates a flow chart of an exemplary method for training muscular activity of patient's still needing at least partial breathing support according to an advantageous embodiment of the invention, where the training session is begun in step 180. In step 182 desired target range of at least one indicator (such as for an indicator of $O_2$-consumption) for the patient is set, after which also desired target time period for breathing support change can be set in step 184. Next in step 186 ventilator applied breathing support is changed with a step, either decreased or increased, which depends on the situation. Typically at the beginning of the training the breathing support is decreased.

Whether the period set in step 184 is not elapsed in step 188, the method is continued in step 190, where value of the indicator is measured and the measured indication value is compared with desired target range (set in step 182) in step 192. If the indicator is in the allowable range in step 194, the method is continued again in step 188. Otherwise, if the indicator is not in the allowable range in step 194, breathing support is continued in step 186, where ventilator applied breathing support is changed in order to normalize the situation. At this stage the breathing support may be either increased or decreased depending on the direction the measured indicator value deviates from the target range.

However, if the period has elapsed in step 188, the training session is stopped in step 196.

The purpose of the measuring period in the previous embodiments is e.g. to ensure that the indications of gas exchange values would become even, and also to allow patient to stabilize for the new ventilation after previous change in ventilator setting.

This time may vary depending on the protocol, but e.g. in a breathing support reduction trial the period could be 10 minutes. In an (exercising) embodiment of the invention, where the patient is trained, the length of the period can be varied in order to train patient's muscular activity and especially the respiratory muscles, and could be even more, e.g. 20 min or 30 min. In this time, when the period is not yet elapsed, indicator(s) can advantageously still be checked continuously.

Amount of the change in ventilator applied breathing support may be e.g. 5 $cmH_2O$ in breathing support reduction trial, or smaller 2-3 $cmH_2O$ in training mode.

It should also be noted in connection with the previous embodiment of the invention that in the breathing support reduction trial (in training or exercising mode) also the target range for the breathing support and/or other indicators, such as a desired target range for the indication of $O_2$-consumption for the patient, maybe re-changed during the procedure according to a certain embodiment of the invention.

In addition it is to be noted that indicators for $VO_2$ and/or $VCO_2$, or alternatively $DO_2$ and $EtCO_2$ are used in connection with the methods described in FIGS. 1A-1C.

Figure 2:
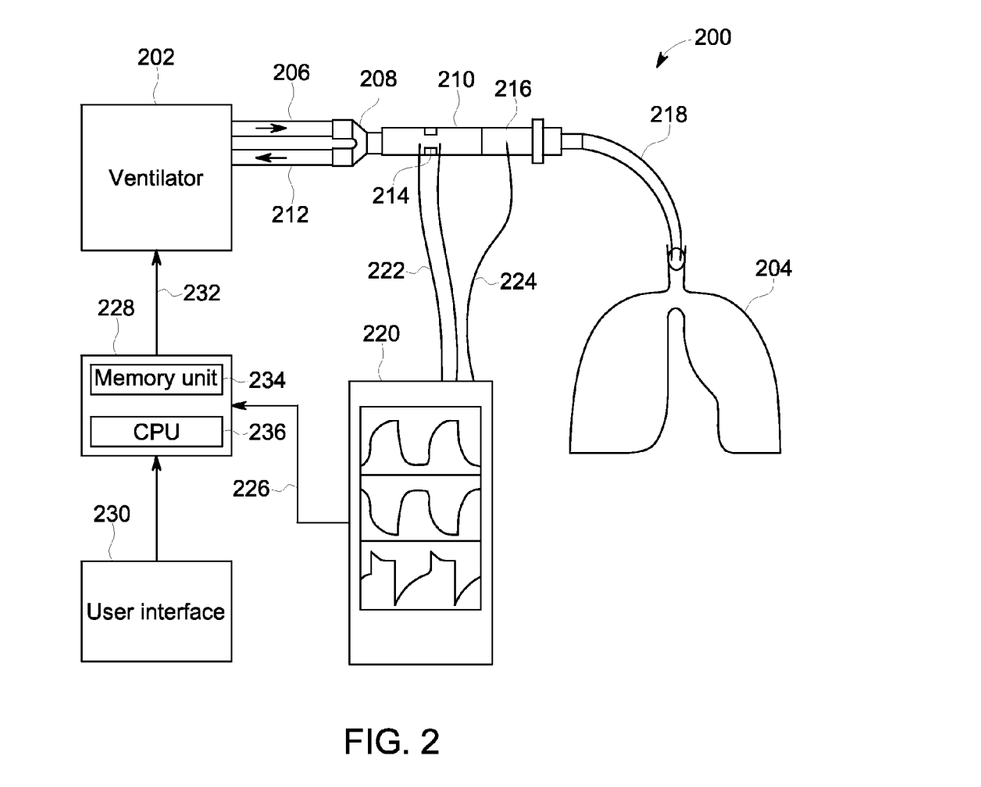
FIG. 2 illustrates a block diagram of an exemplary system for monitoring patient's breathing action response to changes in a ventilator applied breathing support according to an advantageous embodiment of the invention.

FIG. 2 illustrates a block diagram of an exemplary system 200 for monitoring patient's breathing action response to changes in a ventilator applied breathing support according to advantageous embodiment of the invention. The same system can also be used for assessing a readiness of the patient to be weaned from the ventilator 202 in a weaning process, as well as also for training muscular activity of patient's still needing at least partial breathing support, which methods are described in connection with FIGS. 1B and 1C.

In the system the patient is ventilated with a ventilator 202 providing breathing gas to the patient lungs 204 through an inspiration limb 206, Y-piece 208, and patient limb 210 during inspiration phase. During expiration, the breathing gas is exhaled from the lungs 204 through the patient limb 210 to the Y-piece 208 and further to the expiration limb 212 back to ventilator 202.

The patient limb comprises a flow sensor 214, gas sensor 216, and an intubation tube 218. The gas sensor connector may be as well an integral part of the flow sensor 214. Flow signals are transmitted to the monitor 220 through the signal line 222, whereas gas signals are transmitted to the monitor 220 through the signal line 224. These lines may be either pneumatic or electric depending of the flow sensor type.

The monitor (or other component of the system) may comprise data processing unit being adapted to analyse the measured signals in order to determine the index parameters for ventilation control. These index parameters may include oxygen consumption ($VO_2$), carbon dioxide elimination ($VCO_2$), end-tidal $O_2$ concentration ($EtO_2$), inspired $O_2$ concentration ($FiO_2$), end-tidal $CO_2$ concentration ($EtCO_2$), and inspired $CO_2$ concentration ($FiCO_2$). These concentrations may be expressed as volume % of gas or as partial pressure (e.g. in kPa or in mmHg), for example.

The index parameter is further sent through signal line 226 to a controller 228, which is adapted to compare the signal values with the target values, which are either constant values of the controller or given by the user through a user interface 230. The user interface may comprise a keyboard and/or mouse or other data inputting means. From this comparison, and from the time elapsed from the previous breathing support change the controller 228 is adapted to calculate the next breathing support value and transmit this to the ventilator 202 through the signal line 232.

According to an embodiment the controller may also comprise data processing unit, such as a memory unit 234 and CPU 236 connected to each other and also to the user interface means 230. The controller may also be adapted to determine a desired target range for an indication of $O_2$-consumption for the patient. The ventilator 202 is advantageously adapted to change the ventilator applied breathing support according to the instructions of the controller. In addition the system is adapted to repeat at least the steps of the method: b) changing the ventilator applied breathing support, c) measuring the indication of $O_2$-consumption of said patient, and d) comparing the measured indication of $O_2$-consumption of said patient with the desired target range, in order to maintain the measured indication of $O_2$-consumption of said patient within the desired target range.

In addition the system comprises means for checking the measuring period whether it is elapsed or not, where the length of the measuring period depends on the mode or the protocol, such as is the mode a breathing support reduction trial or assessing of the weaning.

Moreover, according to an embodiment of the invention the system is adapted to check the indicators continuously so that if at least one indicator is out of the preset level, the system is adapted to change the breathing support immediately in order to normalize the situation. The system is also adapted to suggest consideration of weaning, when the minimum support pressure is reached and the indicators are still in the desired range, as described in connection of the corresponding method in FIG. 1B Furthermore according to an embodiment of the invention, the system 200 may be adapted to compare an indication of $CO_2$-production of the patient to indication of $O_2$-consumption of said patient, and if said indications reveal $O_2$-consumption growing faster than $CO_2$-production, when decreasing the breathing support for the patient, the systems is adapted to suggest continuing the breathing support for the patient.

Still the system may be adapted to measure said indication of $O_2$-consumption of the patient as an absolute value of $O_2$-consumption ($VO_2$). The system is also adapted to measure according to an embodiment an indication of $O_2$-consumption and/or indication of $CO_2$-elimination of the patient from breathing gases of said patient by integrating the product of the breathing gas flow and gas concentration over time.

In addition an indication of $O_2$-consumption of the patient is a difference ($DO_2$) of inspired $O_2$ ($FiO_2$) and end-tidal $O_2$-concentration ($EtO_2$), whereupon the system 200 is adapted to measure indication of $CO_2$-elimination ($VCO_2$) of the patient as end-tidal $CO_2$-concentration ($EtCO_2$), and adapted to use a combination of high $DO_2$ and high $EtCO_2$ as a predictor of patient's inability to maintain sufficient breathing and suggest immediate increase of the support pressure based on said combination of high $DO_2$ and high $EtCO_2$.

Figure 3:
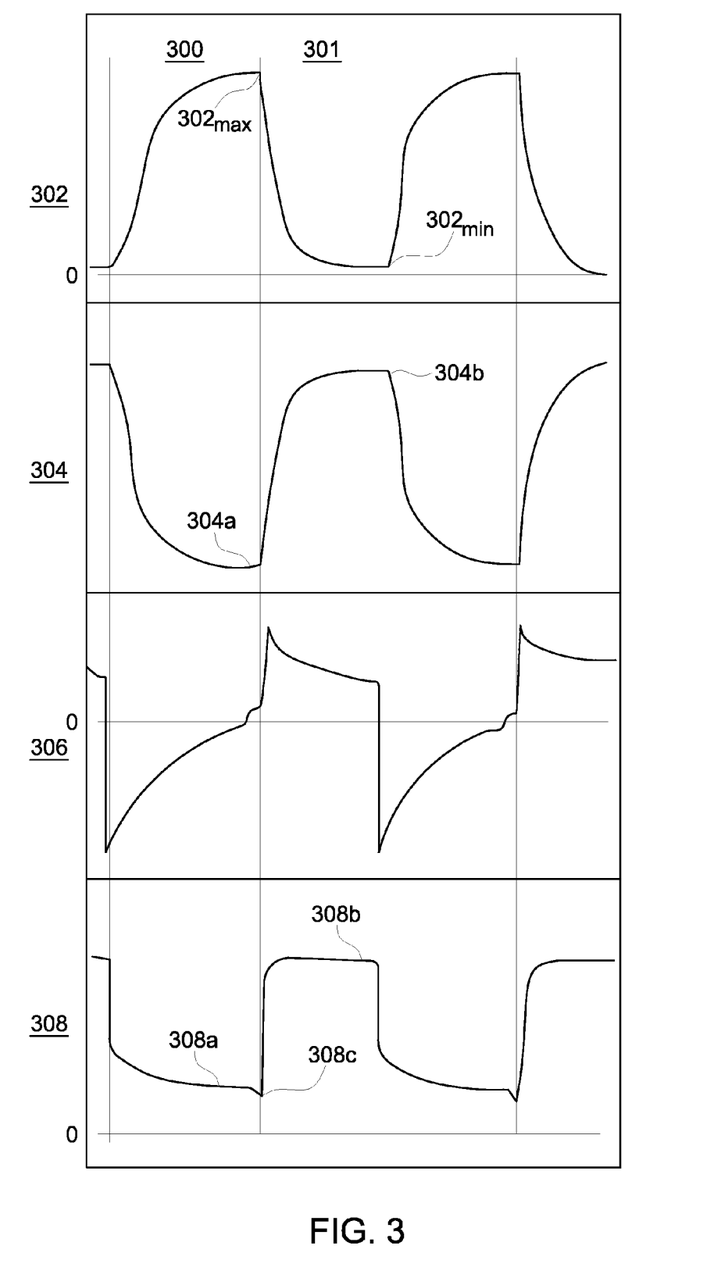
FIG. 3 illustrates exemplary graphs of measured physiological ventilation signals used in monitoring patient's breathing action response to changes in a ventilator applied breathing support according to an advantageous embodiment of the invention.

FIG. 3 illustrates exemplary graphs 302, 304, 306, 308 of measured physiological ventilation signals used in monitoring patient's breathing action response to changes in a ventilator applied breathing support according to an advantageous embodiment of the invention. Expiration and inspiration phases are indicated as phases 300 and 301 respectively.

Graph 302 presents 2 breaths of $CO_2$ waveform. The maximum value $302_{max}$ occurs at the end of expiration 300 and is assigned to $EtCO_2$. $FiCO_2$ $302_{min}$ is determined as minimum value during inspiration 301, or alternatively an average over the inspiration phase.

Waveform 304 presents $O_2$ concentration. $EtO_2$ 304a and $FiO_2$ 304b are determined as the minimum $O_2$ concentration of the breath and average during inspiration respectively.

Graph 306 is the flow waveform. Integrating momentary product of $O_2$ and flow over time gives $O_2$ consumption, $VO_2$. Respectively, $VCO_2$ is calculated by integrating product of $CO_2$ and flow over time. For weaning trial, these index values can either be compared with target values, or alternatively initial values are recorded before the trial, and after the trial values are compared with those. Conclusion is then derived from the rate of change of the index values related to the breathing support reduction.

Graph 308 is the pressure waveform of pressure support ventilation. 308a represents positive end-expiratory pressure (PEEP) and the inspiration pressure. Inspiration support pressure is the difference of the two. 308c indicates a notch at the pressure curve representing the spontaneous breathing action of the patient. Ventilator detecting this notch triggers the breathing support showing as the inspiration support pressure. Another common method to detect the spontaneous action is to detect changes in the patient flow.

Whereas this description concentrates on determining separate parameters and deriving conclusions from comparison to target values, the index may be first calculated by combination of the values, like calculating $VCO_2/VO_2$, or $EtCO_2/DO_2$, and derive the threshold value for the derived index.

Figure 4:
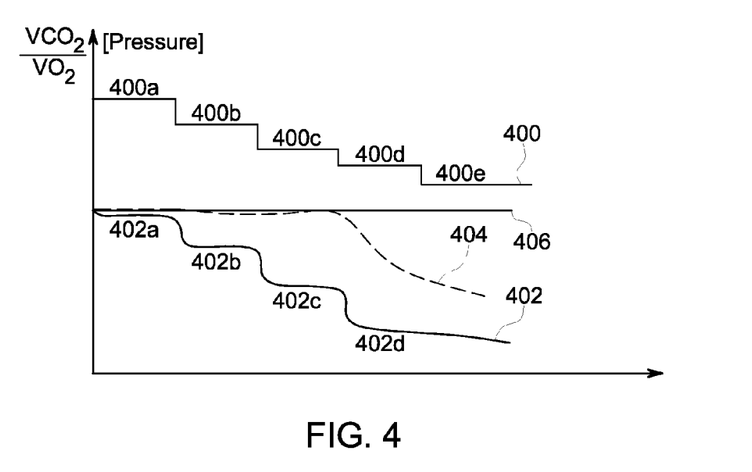
FIG. 4 illustrates exemplary graph of a ratio of $CO_2$-production and $O_2$-consumption as function of decreased breathing support according to an advantageous embodiment of the invention for a patient who is not able to maintain normal ventilation.

FIG. 4 illustrates two exemplary graphs 402, 404 of a ratio of $CO_2$-production ($VCO_2$) and $O_2$-consumption ($VO_2$) as function of decreased breathing support according to advantageous embodiment of the invention for a patient who is not able to maintain normal ventilation and also a graph 406 for a healthy patient.

At first the breathing support (line 400 illustrates a change of a pressure) pressure may be for example 20 cmH$_2$O (over the PEEP) 400a, whereupon the ratio of $VCO_2/VO_2$ is at the normal level 402a. When the breathing support is decreased by a step (for example 5 cmH$_2$O), a change in the ratio of $VCO_2/VO_2$ for the patient being not able to maintain normal ventilation may be noticed 402b. Again, if the breathing support is still decreased (400b, 400c, 400d, 400e), the ratio of $VCO_2/VO_2$ will be changed (402b, 402c, 402d), because $O_2$-consumption ($VO_2$) for a patient being not able to maintain normal ventilation increases more rapidly than $CO_2$-production ($VCO_2$) when the patient tries to maintain his/her breathing in a certain level. At the same time the ratio of $VCO_2/VO_2$ 406 is essentially constant for the healthy patient.

Although the figure presents the breathing support changes as steps, the change may be also more gradual, like linear breath to breath change. In such continuous change, it is however desirable that the change speed is slow enough to allow time for the patient response to follow the breathing support change.

If the patient is able to maintain the ratio of $VCO_2/VO_2$ essentially constant (406) even with predetermined target support pressure level, weaning from breathing support may be considered. This predetermined target pressure may be e.g 0-5 $cmH_2O$ over PEEP, which must not be higher than 10 $cmH_2O$, preferably 5 $cmH_2O$ or lower. Some ventilator support may be accepted for intubated patients since the flow resistance of the endotracheal tube is higher than open airway, and if the patient maintains breathing through the tube with minor support, he likely maintains without support without the tube.

However, a certain type patient may also exists, who can maintain his/her normal ventilation during decreasing the breathing support but in a certain level the ratio of $VCO_2/VO_2$ may dropped (see graph 404)

Figure 5:
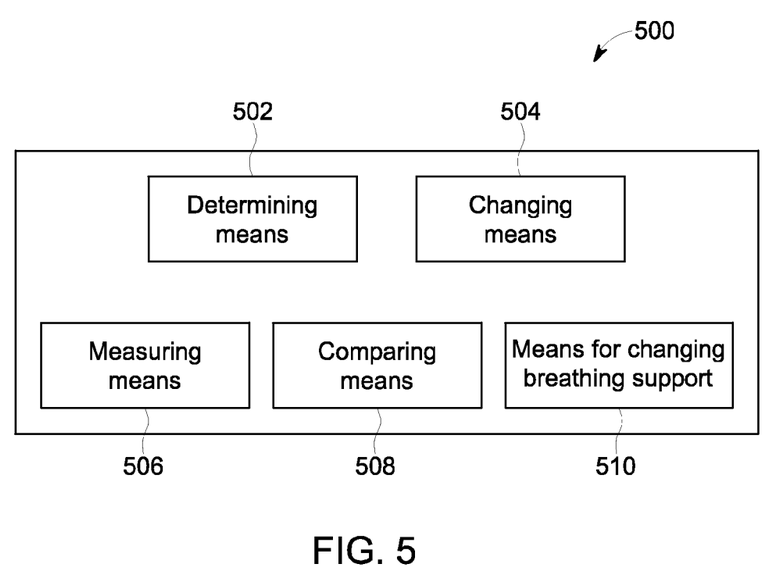
FIG. 5 illustrates an exemplary computer program product for assessing a readiness of a patient to be weaned from a ventilator in a weaning process according to an advantageous embodiment of the invention.

FIG. 5 illustrates an exemplary computer program product 500 for monitoring patient's breathing action response to changes in a ventilator applied breathing support, where the computer program product comprises at least the following code means, such as a determining means 502 for determining a desired target range for an indication of $O_2$-consumption for the patient, changing means 504 for changing the ventilator applied breathing support, measuring means 506 for measuring the indication of $O_2$-consumption of said patient, and comparing means 508 for comparing the measured indication of $O_2$-consumption of said patient with the desired target range. Moreover the computer program product may comprise means 510 for changing ventilator applied breathing support at least until the measured indication of $O_2$-consumption of said patient is again within the desired target range, if it has been outside the desired target range. In addition the determining means 502 may be used also for changing the desired target range.

These means are adapted to perform their function, when said computer program product 500 comprising said means is in run on a computer.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The invention claimed is:

1. A method for monitoring a patient's breathing action response to a ventilator applied breathing support, the method comprising:
    a) determining a desired target range for a breathing gas indication of O2-consumption for the patient;
    b) changing the ventilator applied breathing support;
    c) measuring the breathing gas indication of O2-consumption of said patient;
    d) comparing the measured breathing gas indication of O2-consumption of said patient with the desired target range;
    e) determining breathing gas indication of CO2-elimination of the patient; and
    f) using as data processing unit to compare said breathing gas indication of CO2-elimination of the patient to said breathing gas indication of O2-consumption of said patient, and if said indications reveal O2-consumption growing faster than CO2-elimination when decreasing the breathing support for the patient, suggesting to continue the breathing support for the patient.

2. A method according to claim 1, wherein the method further comprises:
    using a comparison result of step d) and repeating steps b)-d) to maintain breathing gas indication of O2-consumption within said desired target range.

3. A method according to claim 1, wherein the method is used for assessing a readiness of a patient to be weaned from a ventilator in a weaning process, the method further comprising:
    in step b), decreasing the ventilator applied breathing support, whereupon either
        (i) repeating steps b) to d) in so far as the measured breathing gas indication of O2-consumption of said patient is within the desired target range determined in step a), and the ventilator applied support is needed; or
        (ii) if the measured breathing gas indication of O2-consumption of said patient is outside the desired target range determined in step a), increasing the ventilator applied breathing support.

4. A method according to claim 3, wherein the breathing gas indication of O2-consumption of the patient is a difference of inspired O2 and end-tidal O2-concentration and a breathing gas indication of CO2-elimination of the patient is measured as end-tidal CO2-concentration, whereupon a combination of high DO2 and high EtCO2 is used as a predictor of patient's inability to maintain sufficient breathing and immediate increase of the support pressure is suggested.

5. A method according to claim 1, further comprising:
    adjusting the ventilator applied support; and
    repeating at least the steps b)-d) to maintain the breathing gas measured indication of O2-consumption of said patient within the desired target range.

6. A method according to claim 1, wherein said breathing gas indication of O2-consumption of the patient is a difference of inspired O2 and end-tidal O2-concentration.

7. A method according to claim 1, wherein said breathing gas indication of O2-consumption of the patient is measured from breathing gases of said patient by integrating the product of the breathing gas flow and gas concentration over time.

8. A method according to claim 1, further comprising:
    measuring said breathing gas indication of CO2-elimination of the patient is measured as end-tidal CO2-concentration.

9. A method according to claim 1, further comprising:
    measuring said breathing gas indication of O2-consumption of the patient from breathing gases of said patient by integrating the product of breathing gas flow and gas concentration over time.

* * * * *

UNITED STATES PATENT AND TRADEMARK OFFICE
CERTIFICATE OF CORRECTION

PATENT NO. : 8,561,612 B2  
APPLICATION NO. : 12/052174  
DATED : October 22, 2013  
INVENTOR(S) : Heinonen Page 1 of 1

It is certified that error appears in the above-identified patent and that said Letters Patent is hereby corrected as shown below:

In the Claims:

In Column 10, Line 8, in Claim 1, delete "as data" and insert -- a data --, therefor.

Signed and Sealed this
Eleventh Day of February, 2014

Michelle K. Lee
*Deputy Director of the United States Patent and Trademark Office*